United States Patent [19]
Gellert

[11] 4,085,753
[45] Apr. 25, 1978

[54] DISPOSABLE DIAPER WITH INTEGRAL DISPOSAL BAG

[75] Inventor: Dale Albert Gellert, Aurora, Ind.

[73] Assignee: The Procter & Gamble Company, Cincinnati, Ohio

[21] Appl. No.: 567,896

[22] Filed: Apr. 14, 1975

Related U.S. Application Data

[63] Continuation of Ser. No. 498,268, Oct. 20, 1965, Pat. No. 3,877,432.

[51] Int. Cl.² .............................................. A61F 13/16
[52] U.S. Cl. ...................................... 128/284; 128/287
[58] Field of Search ................... 128/284, 287, 290 R

[56] References Cited

U.S. PATENT DOCUMENTS

| | | | |
|---|---|---|---|
| 2,494,307 | 1/1950 | Niolon | 128/284 |
| 2,685,879 | 8/1954 | Emmet | 128/287 |
| 2,699,170 | 1/1955 | Morin | 128/287 |
| 3,024,788 | 3/1962 | Lane | 128/285 |
| 3,036,573 | 5/1962 | Voigtman et al. | 128/287 |
| 3,230,956 | 1/1966 | Kargul | 128/290 R |
| 3,274,999 | 9/1966 | Robinson | 128/290 R |
| 3,295,526 | 1/1967 | Sabee | 128/287 |
| 3,369,545 | 2/1968 | Wanberg | 128/287 |
| 3,554,195 | 1/1971 | Murdoch | 128/287 |
| 3,563,242 | 2/1971 | Hedstrom | 128/287 |
| 3,578,155 | 5/1971 | Small et al. | 128/287 |
| 3,585,999 | 6/1971 | Wanberg | 128/287 |
| 3,604,423 | 9/1971 | Fraser | 128/290 R |
| 3,731,689 | 5/1973 | Schaar | 128/287 |
| 3,865,110 | 2/1975 | Traverse | 128/284 |
| 3,877,432 | 4/1975 | Gellert | 128/287 |

*Primary Examiner*—John D. Yasko
*Attorney, Agent, or Firm*—Elliot A. Lackenbach; John V. Gorman; Richard C. Witte

[57] ABSTRACT

A disposable diaper having an absorbent pad attached to one face of a fluid-impervious back sheet formed from two plies of fluid-impervious material which are united along at least two opposed edges. The two-ply back sheet serves as a disposal bag or sheath within which the used diaper can be encased by turning the back sheet inside out to fully enclose the soiled diaper therewithin.

1 Claim, 7 Drawing Figures

U.S. Patent   April 25, 1978   Sheet 1 of 2   4,085,753
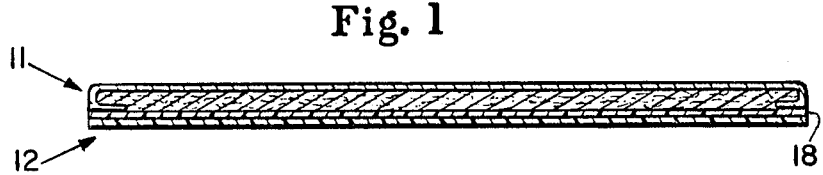
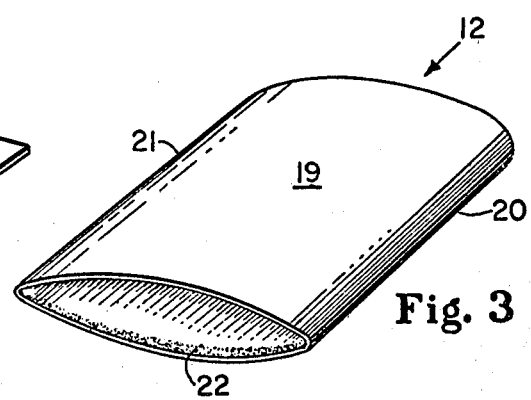
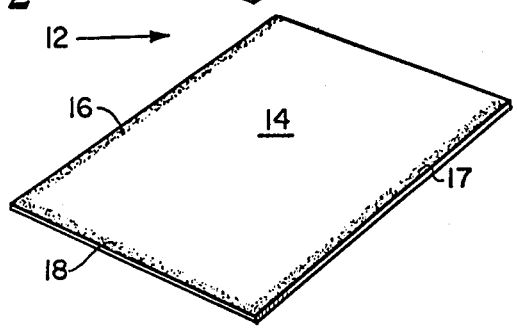
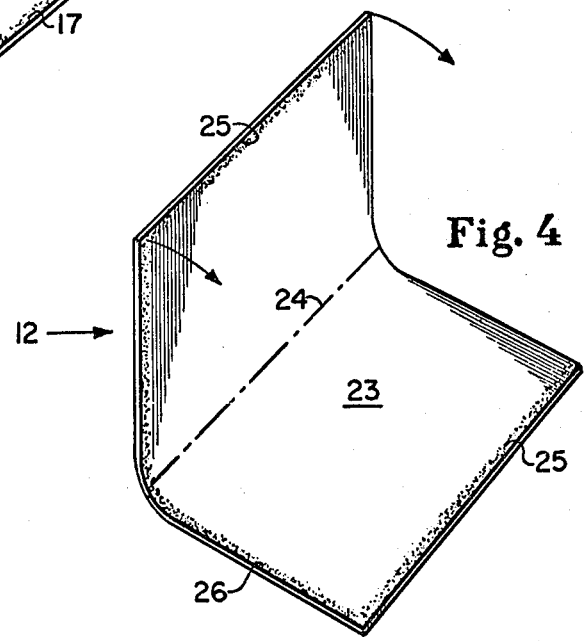

DISPOSABLE DIAPER WITH INTEGRAL DISPOSAL BAG

This application is a continuation of my prior application, Ser. No. 498,268, filed Oct. 20, 1965 now U.S. Pat. No. 3,877,432.

This invention relates to a disposable diaper and more particularly to a disposable diaper incorporating a dual purpose waterproof backsheet adapted to serve as a disposal bag following use of the diaper.

When traveling extensively with an infant in an automobile, it is common practice for parents to use disposable rather than cloth diapers for diapering the child. This is done in order to eliminate the need of washing soiled cloth diapers since cloth diapers are too expensive to be discarded. Another problem which is eliminated is that associated with the storage of the soiled diapers until such time as the parent is conveniently able to launder them — frequently for a protracted period of time. However, even when using disposable diapers on such trips, some inconvenience is experienced since rather than litter the countryside it is necessary to wait to change diapers in a place at which the soiled diaper can be discarded or, alternatively, temporarily store the soiled diaper until such place is reached. The first alternative is not practical since there are times at which diapers should definitely be changed immediately and a conscientious parent cannot postpone the change to a more convenient time and place. The second alternative involves maintaining a wet, frequently objectionably smelling, device inside the automobile.

In connection with the use of disposable diapers in the home, there are circumstances under which it is not possible to dispose of soiled diapers by means of the plumbing system. For example, where a small septic system is being used or where the physical size of the diaper prohibits such disposal. In such cases it is difficult to properly store the soiled diapers with other trash for disposal.

It is an object of the present invention to obviate the above problems.

It is another object of the present invention to provide a disposable diaper incorporating a waterproof backsheet which may be conveniently converted to a disposal bag subsequent to use.

Briefly stated, in accordance with one aspect of this invention, there is provided a disposable diaper comprising an absorbent pad affixed to one face of a protective backsheet. The backsheet comprises two superposed generally rectangular plies of a substantially liquid impermeable web, the plies being united along at least two oppositely disposed edge portions. Each of the plies is free from one another inward of the edge portions and along adjacent third edges which connect corresponding ends of the edge portions, whereby the diaper is adapted to be turned inside out through the opening formed between the third edges of the plies to thus facilitate disposal by encasing the soiled pad within a sheathing formed by the plies.

While the specification concludes with the claim particularly pointing out and distinctly claiming the subject matter which is regarded as forming the present invention it is believed that the invention will be better understood from the following description taken in connection with the accompanying drawings in which:

FIG. 1 is a vertical longitudinal sectional view of a disposable diaper of the present invention.

FIG. 2 is a perspective view illustrating one embodiment of the backsheet of the present invention;

FIG. 3 is a perspective view of another embodiment of said backsheet;

FIG. 4 is a perspective view of a further embodiment of said backsheet; and

Figure 5A:
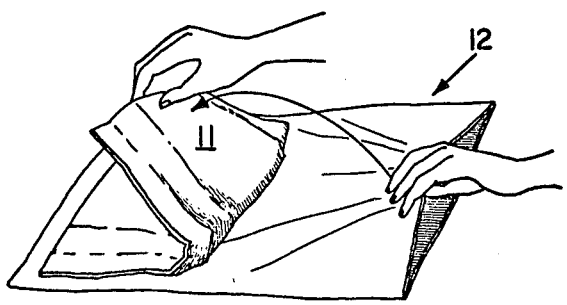
FIGS. 5a, 5b and 5c are perspective views illustrating the manner in which a soiled disposable diaper of the present invention may be pulled inside out following use.

Referring to FIG. 1, there is shown a vertical cross-sectional view of a disposable diaper incorporating the present invention. The diaper comprises an absorbent pad, generally referred to by reference numeral 11, and which is affixed, by adhesive or otherwise, to a protective backsheet 12. The pad construction may, for example, be substantially along the lines described in U.S. Pat. No. 3,180,335 which issued to R. C. Duncan et al. on Apr. 27, 1965 for "Disposable Diaper." In any event the specific construction of the absorbent pad is not important in connection with the disclosure of the subject invention.

The backsheet 12 comprises two plies of a substantially liquid impermeable web such as low density, opaque polyethylene film and is sufficiently large relative to the pad to prevent the pad from extending over the edges of the backsheet. Preferably, the ends of the backsheet 12 extend beyond the ends of the pad 11 to facilitate closure of the self-contained disposal bag, as will be more fully understood from later description. While most commercially available thicknesses of polyethylene film are acceptable for service as the backsheet material, it is most advantageous (from the standpoint of economy and performance characteristics of the diaper) to use plies which have a thickness in the range of from about 0.3 to about 0.8 mils. Preferably the composite thickness of two plies of such material should be between about 0.7 to about 1.4 mils to give the soft, rattle-free, compliant properties which are desirable in a disposable diaper. It should be noted in this connection that the aforesaid properties of a two-ply backsheet 12 will be improved with respect to those of a single backsheet having a thickness equal to the combined thicknesses of the two-ply system.

The backsheet 12 may be constructed of two separate rectangular sheets such as those illustrated in FIG. 2. In this embodiment, the sheets 13 and 14 of ½ mil opaque polyethylene are united to one another in superposed relationship along at least two oppositely disposed side edge portions, as indicated by the longitudinally extending stippled areas 16 and 17 of FIG. 2. The plies are free from one another in the areas thereof intermediate the stippled areas 16 and 17. If desired, the plies may also be united along end edge portion 18 intermediate corresponding ends of edge areas 16 and 17 so as to seal the plies together on three sides. The uniting of ply 13 with ply 14 may be accomplished by heat-sealing, solvent sealing, adhesives, or by any other means which results in a substantially moisture-impervious joint.

Although it is not an absolute necessity, it is highly desirable to prevent "blocking" (sticking together) of the plies in the contiguous face areas thereof inward of the united edge portions. This is achieved by adding an anti-blocking material when formulating the web or, alternatively, by introducing fine particulate matter such as talc, cornstarch or other like substance as a non-integral anti-blocking material between the plies 13 and 14. The former such material may comprise fatty amides, e.g., oleamide, stearamide and behenamides, or other well known anti-blocking additives. Non-integral anti-blocking material can be applied by any convenient means, for example, by hand sprinkling subsequent to the uniting of the plies, by introduction through the extrusion mandrel on blown films, or by mechanical shakers or the like on cast film. Where the plies must be united, as by heat sealing, the anti-blocking material must not interfere with that operation. The employment of an anti-blocking material is not so important, however, where one or both plies are separately embossed to prevent extensive intimate contact.

Alternative forms of backsheet construction are illustrated in FIGS. 3 and 4. FIG. 3 discloses an embodiment of backsheet constructed from a plastic film such as ½ mil opaque polyethylene which is extruded in tubular form and has a transverse circumference equal to twice the width of the backsheet 12. A length 19 of the tubular film is cut and usable in that condition as an open-ended backsheet 12. In this case, the plies which constitute the backsheet 12 are integrally united on oppositely disposed edge portions, the longitudinal folds 20, 21, of the length 19. If desired, the length 19 could also be sealed along end edge 22 whereby to form an envelope-like structure the interior of which is accessible only along one edge.

The embodiment of FIG. 4 illustrates a backsheet which is formed from a single sheet 23 of a suitable plastic film having a length approximately double the width of the backsheet 12. The sheet 23 is folded along line 24 as illustrated and the superposed plies thereof united along the stippled areas 25 of the edges oppositely disposed from the fold line 24. Thus there is formed an open-ended double ply structure in which two opposed edge portions are united, one integrally along line 24 and the other along areas 25 by the means suggested above. Alternatively, the plies can also be united along the stippled area 26 whereby to form a three-sided enclosure. If desired, an anti-blocking agent can be introduced between the plies of the backsheets of FIGS. 4 and 5.

Figure 5B:
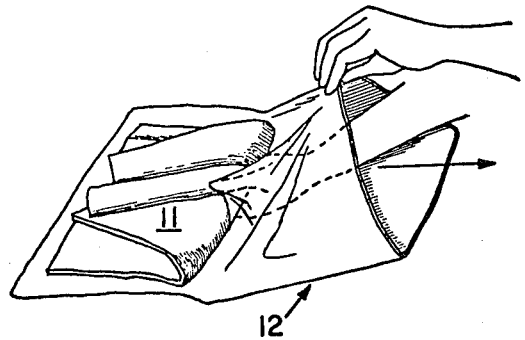
Figure 5C:
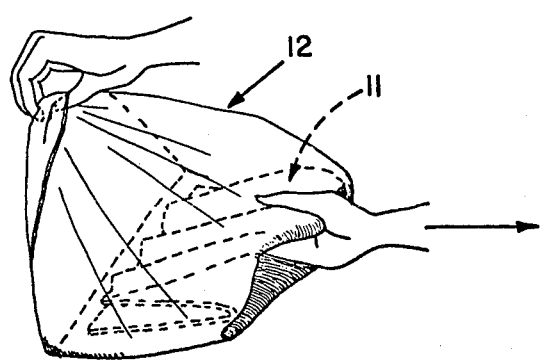

Referring to FIGS. 5a, 5b and 5c there is illustrated the manner in which a soiled disposable diaper incorporating the backsheet 12 of the present invention can be manipulated so as to permit one to pull the unit inside out and thereby enclose the soiled pad in a waterproof bag. This operation begins as shown in FIG. 5a in which the soiled pad 11 is loosened at the end thereof adjacent a pair of unsealed edges of the backsheet 12 and the loosened half of the pad folded over the balance of the pad. Next, the plies which comprise the backsheet are separated along an unsealed edge and one hand is inserted (see FIG. 5b) between the plies and brought to the center (crotch area) of the diaper. The soiled pad 11 and the upper ply of the backsheet 12 are simultaneously grasped in the center area by the one hand while the other hand grasps the open, unsealed edge of the upper ply. Then the one hand pulls the center area towards and through the unsealed edge while the other hand holds the upper ply, as shown.

Thus the inner surfaces of the backsheet 12 (i.e., at least those of the portion of the plies intermediate the center area and the unsealed edge through which the hand is inserted and later withdrawn) is reversed and turned outwardly and the soiled pad 11 is covered by the reversed areas of the backsheet plies. If the backsheet 12 is open on only one edge, that edge may then be closed by any reasonable means, for example, by tying, twisting, taping, folding and clipping or the like. Where the backsheet 12 is open-ended, following completion of the above steps both unsealed edges will be adjacent and can, if desired, be simultaneously closed as suggested above to maintain the pad 11 inside. From the standpoint of containment subsequent to the inversion of the soiled diaper, the form of backsheet in which the plies are sealed along three edges, leaving one pair of edges unsealed, is preferred since this structure provides a more positive closure for one end of the backsheet and facilitates handling of the inverted diaper and securement of the other end of the backsheet.

Alternatively, the user can reach through the open side of the two ply backsheet, grasp the opposite end of the backsheet and pad and pull the entire unit inside out to thereby enclose the soiled pad. However, this is less desirable since such a procedure involves more effort and increases the possibility of dropping excreted matter during the reversing process.

Many modifications of the above invention may be used and it is not intended to hereby limit it to the particular embodiments shown or described. The terms used in describing the invention are used in their descriptive sense and not as terms of limitation, it being intended that all equivalents thereof be included within the scope of the appended claim.

For example, within the scope of my invention is:

A damp resistant diaper ensemble in the configuration of a flat elongated rectangle, said ensemble having a means for manual eversion of a bag to enclose a used damp diaper comprising a diaper having on one half length, at least one adhesive means across the width thereof, a water resistant bag of sheet material of a size substantially coextensive of the diaper and having an opening in a first end portion and attached on the outside surface adjacent its second end portion to said diaper adhesive means, said outside surface of said bag adjacent its opening and the diaper second half being joined by an adhesive tack means to define a disengageable attachment means between the bag and diaper whereby said bag opening defines a hand insertion means so said diaper second half portion may be readily detached from the bag, folded over the remaining first portion to cover the soiled surfaces, and be enclosed in the bag by said manual eversion thereof.

What is claimed is:

1. A damp resistant diaper ensemble in the configuration of a flat elongated rectangle, said ensemble having a means for manual eversion of a bag to enclose a used damp diaper comprising a diaper having on one half length, at least one adhesive means across the width thereof, a water resistant bag of sheet material of a size substantially coextensive of the diaper and having an opening in a first end portion and attached on the outside surface adjacent its second end portion to said diaper adhesive means, said outside surface of said bag adjacent its opening and the diaper second half being joined by an adhesive tack means to define a disengageable attachment means between the bag and diaper whereby said bag opening defines a hand insertion means so said diaper second half portion may be readily detached from the bag, folded over the remaining first portion to cover the soiled surfaces, and be enclosed in the bag by said manual eversion thereof.

* * * * *